(12) United States Patent
Anderson et al.

(10) Patent No.: US 10,716,482 B2
(45) Date of Patent: Jul. 21, 2020

(54) THERMODILUTION CATHETER SYSTEMS AND METHODS FOR DETERMINING BLOOD FLOW RATES

(71) Applicant: HEXACATH, Rueil-Malmaison (FR)

(72) Inventors: James M. Anderson, Corcoran, MN (US); Jan Weber, Maastricht (NL); Steven J Koch, Zimmerman, MN (US); Timothy S. Girton, Edina, MN (US); Nico H J Pijls, Waalre (NL); Bernard De Bruyne, Kraainem (BE)

(73) Assignee: HEXACATH, Rueil-Malmaison (FR)

( * ) Notice: Subject to any disclaimer, the term of this patent is extended or adjusted under 35 U.S.C. 154(b) by 543 days.

(21) Appl. No.: 14/261,139

(22) Filed: Apr. 24, 2014

(65) Prior Publication Data

US 2014/0323887 A1 Oct. 30, 2014

Related U.S. Application Data

(60) Provisional application No. 61/816,022, filed on Apr. 25, 2013.

(51) Int. Cl.
*A61B 5/026* (2006.01)
*A61B 5/028* (2006.01)

(52) U.S. Cl.
CPC .............. *A61B 5/026* (2013.01); *A61B 5/028* (2013.01)

(58) Field of Classification Search
CPC .................................. A61B 5/026; A61B 5/028
See application file for complete search history.

(56) References Cited

U.S. PATENT DOCUMENTS

| 3,545,428 A | 12/1970 | Webster |
| 3,620,207 A | 11/1971 | Sinclair |

(Continued)

FOREIGN PATENT DOCUMENTS

| EP | 1930045 A1 | 6/2008 |
| WO | 2009049823 A1 | 4/2009 |

(Continued)

OTHER PUBLICATIONS

Kenneth O. Hill and Gerald Meltz, Fiber Bragg Grating Technology Fundamentals and Overview, Journal of Lightwave Technology, vol. 15, No. 8, Aug. 1997.

(Continued)

*Primary Examiner* — Eric J Messersmith
(74) *Attorney, Agent, or Firm* — Clark & Body LP

(57) ABSTRACT

Catheter systems and methods for determining blood flow rates based on temperature measurements by thermodilution. The catheter may include a fluid lumen defined between inner and outer tubular members for delivering an indicator fluid, and a guidewire lumen defined by the inner tubular member. The catheter may include fluid infusion openings at the distal end region of the outer tubular member configured to permit the indicator fluid to exit the catheter from the fluid lumen, and a fluid hole located at the distal end region of the inner tubular member configured to permit the indicator fluid to pass from the fluid lumen into the guidewire lumen. A temperature sensor positioned on a guidewire may be positioned within the guidewire lumen to measure the temperature of the indicator fluid entering the guidewire lumen through the fluid hole. A blood flow rate may be calculated based on the measured temperature.

13 Claims, 11 Drawing Sheets

(56) References Cited

U.S. PATENT DOCUMENTS

| | | | |
|---|---|---|---|
| 3,726,269 A | 4/1973 | Webster | |
| 4,153,048 A | 5/1979 | Magrini | |
| 4,576,182 A | 3/1986 | Normann | |
| 5,178,153 A | 1/1993 | Einzig | |
| 5,281,203 A * | 1/1994 | Ressemann | A61M 25/0172 600/585 |
| 6,231,498 B1 | 5/2001 | Pfeiffer et al. | |
| 6,343,514 B1 | 2/2002 | Smith | |
| 6,551,250 B2 | 4/2003 | Khalil | |
| 6,623,436 B2 | 9/2003 | Krivitski et al. | |
| 7,112,176 B2 | 9/2006 | Krivitski et al. | |
| 7,549,965 B2 | 6/2009 | Krivitski et al. | |
| 7,775,988 B2 | 8/2010 | Pijls | |
| 8,133,185 B2 | 3/2012 | Krivitski et al. | |
| 2002/0177783 A1 | 11/2002 | Khalil | |
| 2003/0158490 A1 | 8/2003 | Krivitski et al. | |
| 2003/0158491 A1 | 8/2003 | Krivitski et al. | |
| 2004/0054293 A1 | 3/2004 | Krivitski et al. | |
| 2005/0113798 A1* | 5/2005 | Slater | A61M 25/01 604/508 |
| 2007/0078352 A1* | 4/2007 | Pijls | A61B 5/028 600/504 |
| 2010/0286537 A1 | 11/2010 | Pijls | |
| 2011/0208072 A1 | 8/2011 | Pfeiffer et al. | |
| 2012/0238869 A1 | 9/2012 | Schmitt et al. | |
| 2014/0081134 A1 | 3/2014 | Fortson et al. | |

FOREIGN PATENT DOCUMENTS

| | | | |
|---|---|---|---|
| WO | WO 2009/049823 | * | 4/2009 |
| WO | 2012164481 A1 | | 12/2012 |

OTHER PUBLICATIONS

Marcel Van't Veer, Maartje C.F. Geven, Marcel C.M. Rutten, Arjen Van Der Horst, Wilbert H. Aarnoudse, Nico H.J. Pijls, and Frans N. Van De Vosse, Continuous infusion thermodilusion for assessment of coronary flow: Theoretical background and in vitro validation, Medical Engineering and Physics, Jan. 25, 2009.

Wilbert Aarnoudse, Marcel Van't Veerm Nico H.J. Pijls, Joost Ter Woorst, Steven Vercauteren, Pim Tonino, Maartje Geven, Marcel Rutten, Eduard Van Hagen, Bernard De Bruyne, and Frans Can De Vosse, Direct Volumetric Blood Flow Measurement in Coronary Arteries by Thermodilution, Journal of the American College of Cardiology, Dec. 7, 2007.

* cited by examiner

THERMODILUTION CATHETER SYSTEMS AND METHODS FOR DETERMINING BLOOD FLOW RATES

CROSS-REFERENCE TO RELATED APPLICATIONS

This application claims priority under 35 U.S.C. § 119 to U.S. Provisional Application Ser. No. 61/816,022, filed Apr. 25, 2013, the entirety of which is incorporated herein by reference.

TECHNICAL FIELD

The disclosure is directed to catheter systems and methods for determining blood flow rates in blood vessels, such as coronary arteries. More particularly, the disclosure is directed to systems and methods for determining blood flow rates based on temperature measurements by thermodilution.

BACKGROUND

Thermodilution is a method of determining blood flow through a body vessel based on in vivo measurements of temperature drop of blood using a temperature sensor as a result of introducing an indicator fluid (e.g., saline) having a lower temperature than blood into the blood upstream from the temperature sensor. The measured temperature drop, which is a function of the blood flow and set indicator fluid flow, may be used to determine the absolute blood flow rate through the body vessel. The calculated absolute blood flow rate may be used for the diagnosis and understanding of microvascular disease.

Accordingly, there is a need to provide alternative systems and methods for determining the absolute blood flow rate in blood vessels, such as coronary arteries.

SUMMARY

The disclosure is directed to several alternative designs, materials and methods of manufacturing medical device structures and assemblies, and uses thereof.

Accordingly, one illustrative embodiment is a catheter system for determining blood flow in a body lumen. The system includes a catheter including an outer tubular member and an inner tubular member disposed within the outer tubular member. The catheter also includes a fluid lumen defined between the inner tubular member and the outer tubular member and a second lumen (e.g., a guidewire lumen, a temperature probe lumen, etc.) defined by the inner tubular member. One or more fluid infusion openings are located at a distal end region of the catheter. The one or more fluid infusion openings are configured to permit fluid to exit the catheter from the fluid lumen. Additionally, one or more fluid holes are located at the distal end region of the catheter, and are configured to permit fluid to pass from the fluid lumen into the second lumen. In some instances, the catheter system also includes an elongate member (e.g., a guidewire, a temperature probe, etc.) advanceable through the second lumen of the catheter. The elongate member may include a temperature sensor positioned on a distal end portion of the elongate member which is positionable within the second lumen of the inner tubular member to measure a temperature of fluid entering the second lumen of the inner tubular member through the one or more fluid holes.

Another illustrative embodiment is a catheter system for determining blood flow in a body lumen. The system includes an elongate catheter shaft having a proximal end, a distal end, and a lumen extending therethrough. The catheter shaft also includes one or more fluid infusion openings located at a distal end region of the catheter shaft. The one or more fluid infusion openings are configured to permit fluid to exit the lumen of the catheter shaft into the body lumen. A first temperature sensor is positioned within the lumen of the catheter shaft proximate the one or more fluid infusion openings. The first temperature sensor is configured to be in direct contact with a fluid within the lumen to measure a temperature of the fluid exiting the lumen through the one or more fluid infusion openings. In some instances, the elongate catheter shaft may include an elongated reduced diameter region extending distal of the one or more fluid infusion openings to the distal end of the elongate catheter shaft. A second temperature sensor may be positioned on an exterior of the elongated reduced diameter region proximate the distal end of the elongate catheter shaft to measure a mixture of blood and fluid infused into the blood from the catheter shaft.

Yet another illustrative embodiment is a method of determining blood flow in a body vessel of a patient. The method includes advancing a catheter to a desired location within the body vessel. The catheter includes an outer tubular member, an inner tubular member disposed within the outer tubular member, a fluid lumen defined between the inner tubular member and the outer tubular member, and a second lumen defined by the inner tubular member. A fluid is delivered through the fluid lumen to a distal end region of the catheter. A temperature sensor mounted on an elongate member is positioned within the second lumen of the catheter and the temperature of the fluid passing into the second lumen from the fluid lumen is measured with the temperature sensor positioned in the second lumen. The fluid is infused into blood in the body vessel from the fluid lumen and the temperature of a mixture of the fluid and the blood is measured with a temperature sensor mounted on an elongate member positioned in the body vessel distal of the catheter. The blood flow rate may then be calculated based on the measured temperature of the fluid and the measured temperature of the mixture of the fluid and the blood.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
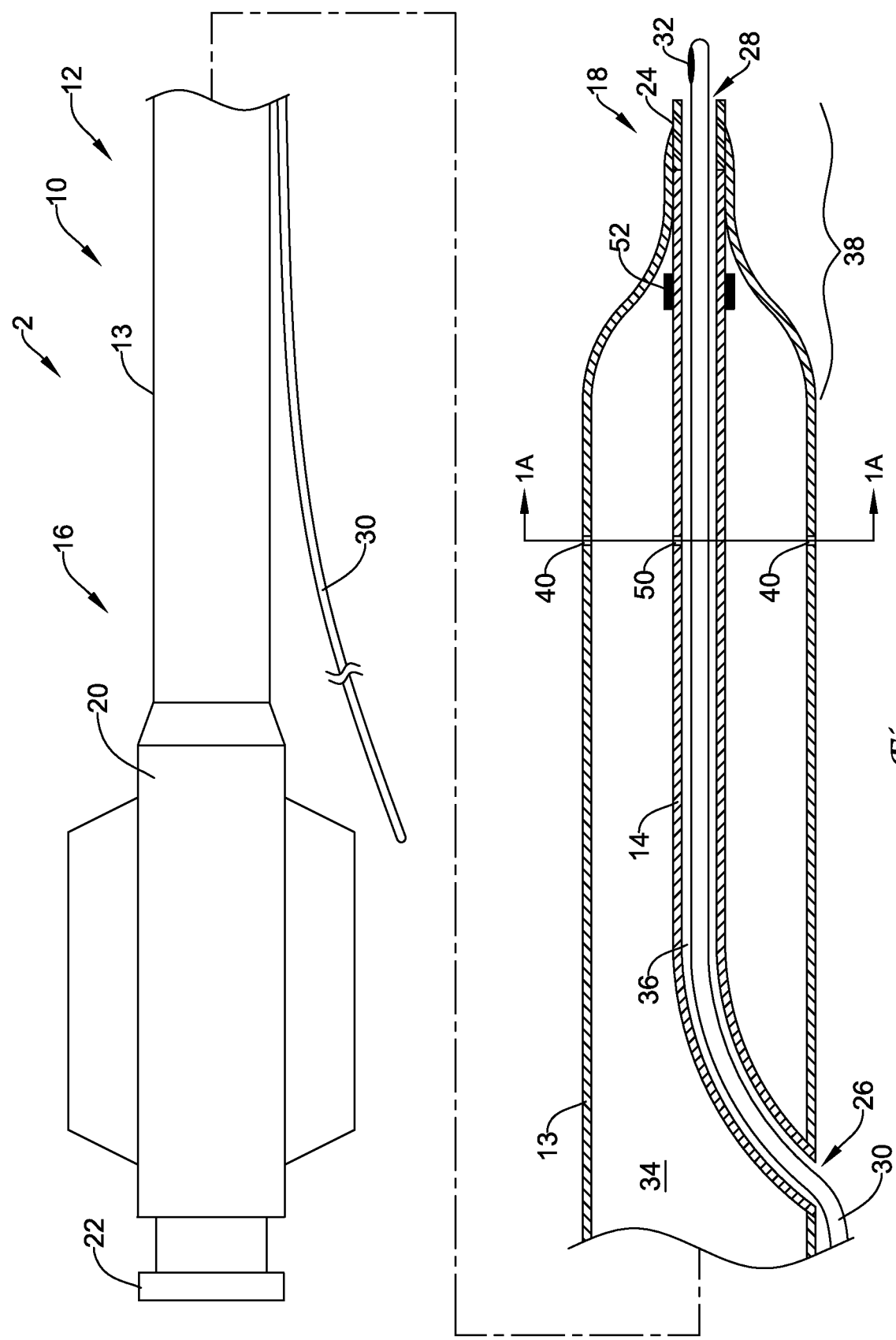
FIG. 1 is a schematic representation of an exemplary catheter system including an infusion catheter and associated guidewire for determining blood flow through a body vessel using a thermodilution technique.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary catheter system 2 including an infusion catheter 10 and associated guidewire 30 for determining blood flow through a body vessel using a thermodilution technique is illustrated in FIG. 1. The infusion catheter 10 may include an elongate catheter shaft 12 extending distally from a hub assembly 20. The catheter shaft 12 may have a proximal end 16 attached to the hub assembly 20 and a distal end 18 opposite the proximal end 16. The catheter shaft 12 may be a dual lumen catheter shaft having a first, infusion fluid lumen 34 and a second, guidewire lumen 36 extending along at least a portion of the catheter shaft 12 configured for advancing the infusion catheter 10 over a guidewire 30. For example, in some embodiments, the catheter 10 may be an over-the-wire (OTW) catheter in which the guidewire lumen 36 may extend through the entire length of the catheter shaft 12 from the distal end 18 to the proximal end 16. However, in other embodiments, such as the embodiment shown in FIG. 1, the catheter 10 may be a single-operator-exchange (SOE) catheter in which the guidewire lumen 36 extends only through a distal portion of the catheter shaft 12.

The catheter shaft 12 may include an outer tubular member 13 and an inner tubular member 14 extending through the lumen of the outer tubular member 13. With the SOE catheter construction of FIG. 1, the infusion fluid lumen 34 may be defined by the outer tubular member 13 through the proximal portion of the catheter shaft 12, while the infusion fluid lumen 34 may be defined between an outer surface of the inner tubular member 14 and an inner surface of the outer tubular member 13 through the distal portion of the catheter shaft 12. In embodiments in which the catheter is an OTW construction, the infusion fluid lumen 34 may be defined between an outer surface of the inner tubular member 14 and an inner surface of the outer tubular member 13 throughout the catheter shaft 12. The hub assembly 20 may include a proximal port 22 in fluid communication with the infusion fluid lumen 34. A source of infusion fluid (not shown), such as an infusion pump, syringe, etc., may be coupled to the proximal port 22 to supply infusion fluid to the infusion fluid lumen 34.

The lumen of the inner tubular member 14 may define the guidewire lumen 36 with a distal guidewire port 28 proximate the distal end of the inner tubular member 14 and a proximal guidewire port 26 proximate the proximal end of the inner tubular member 14. The distal guidewire port 28 may be located proximate the distal end 18 of the catheter shaft 12 and the proximal guidewire port 26 may be located a short distance proximal of the distal end 18 and distal of the proximal end 16 of the catheter shaft 12. The proximal guidewire port 26 may be of any desired construction, providing access to the guidewire lumen 36. For example, in some embodiments the proximal guidewire port 26 may be formed in accordance with an a guidewire port forming process as described in U.S. Pat. No. 6,409,863, which is incorporated herein by reference.

A distal end portion 38 of the outer tubular member 13 may be a reduced diameter portion or necked portion, secured to the inner tubular member 14 to seal the infusion lumen 34 proximate the distal end 18 of the catheter shaft 12. For example, the distal end portion 38 may include a tapered region in which the outer tubular member 13 tapers down to a reduced inner and/or outer diameter at the distal end of the outer tubular member 13. Thus, the inner surface of a distal end portion of the outer tubular member 13 may be secured to the outer surface of a distal end portion of the inner tubular member 14 in the distal end portion 38. The outer tubular member 13 may be secured to the inner tubular member 14, for example, by laser welding, hot jaws, or other thermal bonding method, an adhesive bonding method, or other bonding method if desired.

In some instances, the catheter shaft 12 may include a distal tip 24, formed as a separate component and secured at the distal end 18 of the catheter shaft 12. For example, in some instances the distal tip 24 may be secured to the inner tubular member 14 and/or outer tubular member 13, for example, by laser welding, hot jaws, or other thermal bonding method, an adhesive bonding method, or other bonding method if desired. As shown in FIG. 1, in some embodiments, the distal end portion of the outer tubular member 13 may span the joint between the inner tubular member 14 and the distal tip 24 such that the distal end portion of the outer tubular member 13 is bonded to each of the inner tubular member 14 and the distal tip 24. In other instances, the distal tip 24 may be formed as a unitary portion of the inner tubular member 14 and/or the outer tubular member 13.

The catheter shaft 12 may also include one or more radiopaque markers 52 located proximate the distal end 18 of the catheter shaft 12. The radiopaque marker(s) 52 may facilitate viewing the location of the distal end 18 of the catheter shaft 12 using a fluoroscopy technique or other visualization technique during a medical procedure. In the illustrative embodiment, the catheter shaft 12 includes a radiopaque marker 52 secured to the inner tubular member 14 proximate the tapered distal end portion 38 of the catheter shaft 12.

Figure 1A:
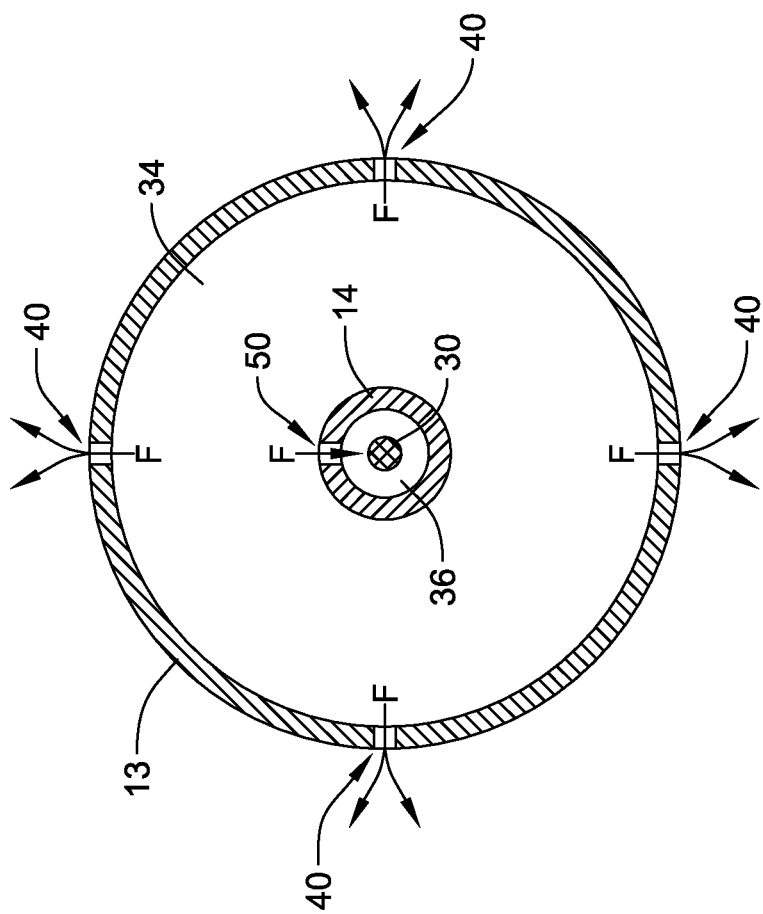
FIG. 1A is a cross-sectional view taken along line 1A-1A of FIG. 1.

The catheter shaft 12 may include one or more fluid infusion openings 40 (e.g., holes, apertures) located at a distal end region of the catheter 10. The fluid infusion openings 40 may be in fluid communication with the infusion fluid lumen 34 and may be configured to permit infusion fluid to exit the catheter 10 from the infusion fluid lumen 34 proximate the distal end 18 of the catheter shaft 12. For example, the catheter shaft 12 may include a plurality of fluid infusion openings 40 extending through a wall of the outer tubular member 13 from an inner surface of the outer tubular member 13 to an outer surface of the outer tubular member 13. As shown in FIG. 1A, in one illustrative embodiment, the catheter shaft 12 may include four fluid infusion openings 40 equidistantly spaced circumferentially around the outer tubular member 13 (i.e., with each fluid infusion opening 40 arranged about 90° from another fluid infusion opening 40. In other embodiments, the catheter shaft 12 may include one, two, three, or more fluid infusion openings 40 arranged around the perimeter of the catheter shaft 12.

The fluid infusion openings 40 may be configured to expel an infusion fluid (e.g., an indicator fluid) in a radially outward direction from each of the fluid infusion openings 40 to facilitate mixing of the infusion fluid with blood flowing through the vessel lumen. In other embodiments, the fluid infusion openings 40 may be arranged in a different orientation, such as in a fashion to permit infusion fluid to be expelled generally distally from the catheter shaft 12, if desired.

Figure 2:
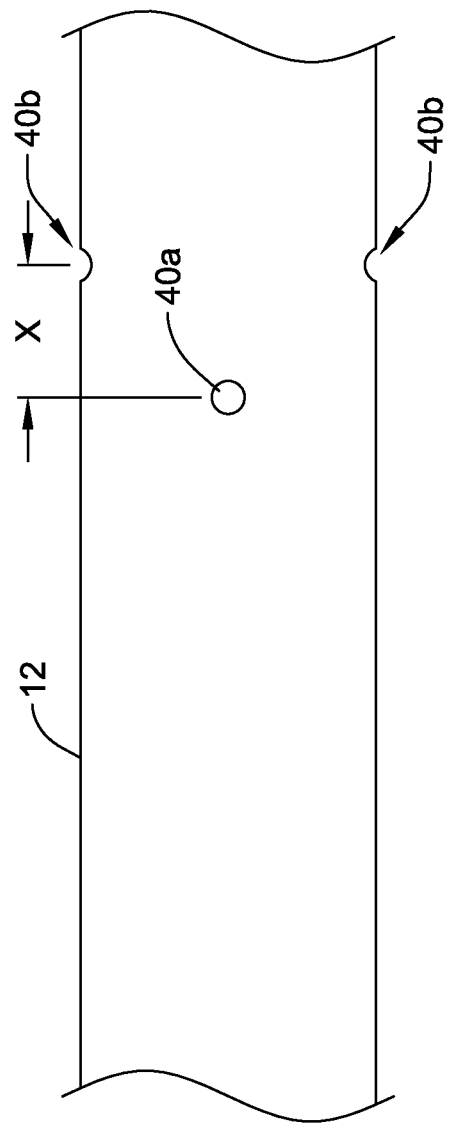
FIG. 2 is a side view of a portion of the infusion catheter of FIG. 1.

As shown in FIG. 2, in some instances one or more of the fluid infusion openings 40 may be longitudinally displaced from one or more of the other fluid infusion openings 40. For example, first and second oppositely positioned fluid infusion openings 40a (only one of which is visible in FIG. 2) may be located a longitudinal distance X, such as about 0.5 millimeters, about 1 millimeter, about 2 millimeters, or about 3 millimeters, away from third and fourth oppositely positioned fluid infusion openings 40b, in some embodiments. In other embodiments, the first and second oppositely positioned fluid infusion openings 40a may be longitudinally aligned with the third and fourth oppositely positioned fluid infusion openings 40b, if desired.

The one or more fluid infusion openings 40 may be configured to generate a jet of infusion fluid F exiting the catheter shaft 12. For example, the fluid infusion openings 40 may be appropriately sized to generate a pressure stream of the infusion fluid F exiting the fluid infusion openings 40. In some instances, the fluid infusion openings 40 may have a diameter of about 25 microns (0.025 millimeters) to about 300 microns (0.300 millimeters), about 25 microns (0.025 millimeters) to about 100 microns (0.100 millimeters), about 100 microns (0.100 millimeters) to about 200 microns (0.200 millimeters), or about 200 microns (0.200 millimeters) to about 300 microns (0.300 millimeters), for example. The size of the fluid infusion openings 40 may be selected based on the volume of infusion fluid to ensure a jet of infusion fluid is formed exiting the catheter shaft 12.

The catheter shaft 12 may also include one or more fluid holes 50 (e.g., openings, apertures) located at the distal end region of the catheter 10. The fluid hole(s) may be in fluid communication with the infusion fluid lumen 34 and may be configured to permit infusion fluid to pass from the infusion fluid lumen 34 into the guidewire lumen 36. For example, the catheter shaft 12 may include one or more fluid holes 50 extending through a wall of the inner tubular member 14 from an outer surface of the inner tubular member 14 to an inner surface of the inner tubular member 14. As shown in FIG. 1A, in the illustrative embodiment the catheter shaft 12 may include one fluid hole 50 extending through the wall of the inner tubular member 14 to permit infusion fluid F to enter the guidewire lumen 36 from the infusion fluid lumen 34. However, in other embodiments the catheter shaft 12 may include two, three or more such fluid holes 50, if desired.

The fluid hole(s) 50 may be a weeping hole configured to allow infusion fluid to weep or exude slowly into the guidewire lumen 36 from the infusion fluid lumen 34. For instance, the fluid hole(s) 50 may be configured to allow infusion fluid to weep, drip, trickle, ooze or otherwise slowly exude into the guidewire lumen 36. In some instances, the fluid hole(s) 50 may have a diameter of about 100 microns (0.100 millimeters) to about 300 microns (0.300 millimeters), about 100 microns (0.100 millimeters) to about 200 microns (0.200 millimeters), or about 200 microns (0.200 millimeters) to about 300 microns (0.300 millimeters), for example.

The catheter system 2 may also include an elongate member, such as a guidewire 30 sized and configured to be disposed through the guidewire lumen 36 of the infusion catheter 10 such that the infusion catheter 10 may be advanced along the guidewire 30 to a target location in the vasculature. The guidewire 30 may include a temperature sensor 32, such as a thermistor or a thermocouple, mounted on a distal end region of the guidewire 30. One illustrative embodiment of a guidewire 30 having a temperature sensor 32 mounted thereon is described in U.S. Pat. No. 6,343,514, which is incorporated by reference herein. In some instances, the guidewire 30 may also include a pressure sensor located at the distal end region of the guidewire 30 for measuring blood pressure at a target location within the vasculature.

Figure 3:
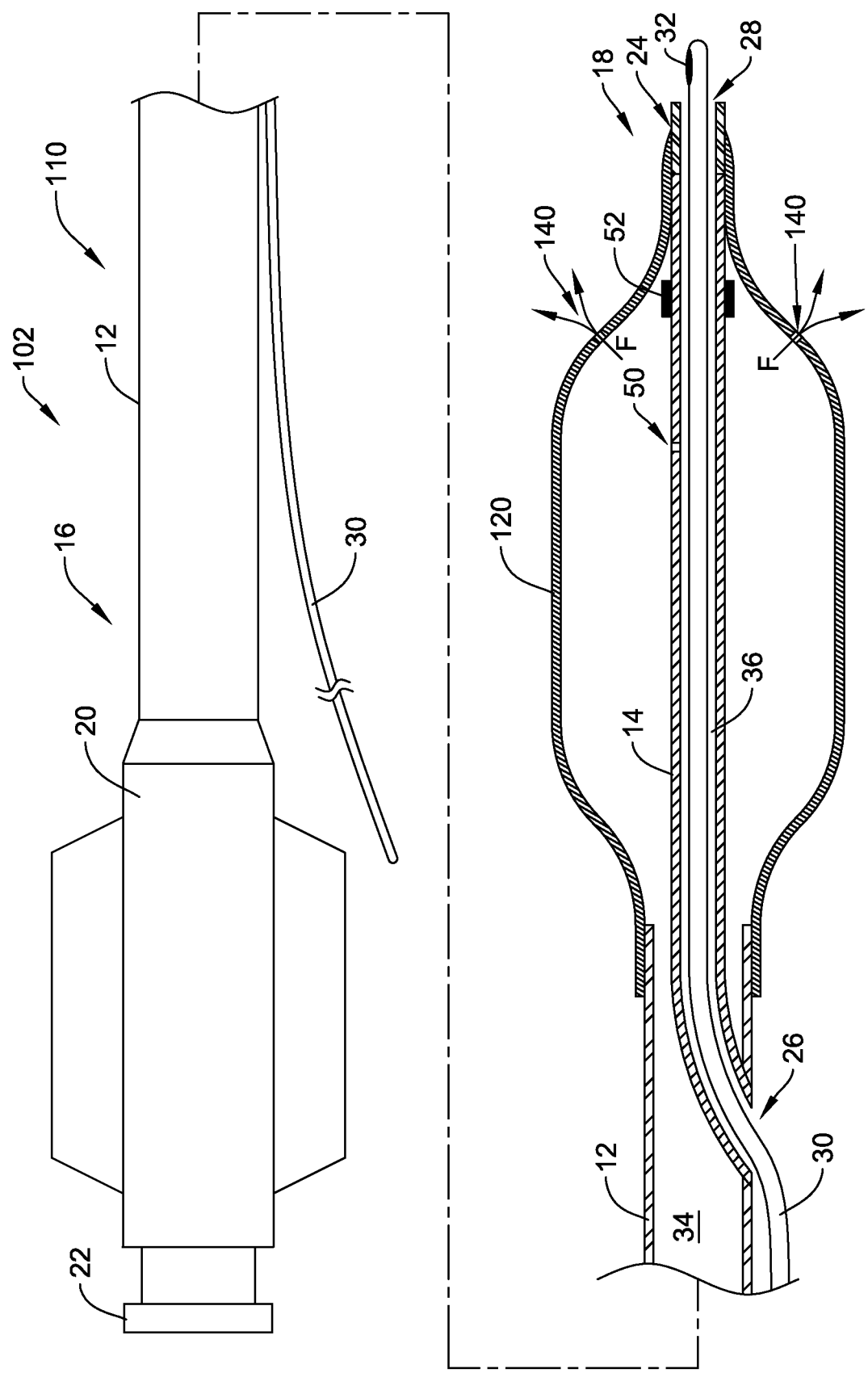
FIG. 3 is a schematic representation of an alternative embodiment of a catheter system including an infusion catheter and associated guidewire for determining blood flow through a body vessel using a thermodilution technique.

Another illustrative catheter system 102 including an infusion catheter 110 and associated guidewire 30 for determining blood flow through a body vessel using a thermodilution technique is illustrated in FIG. 3. In many respects the infusion catheter 110 may be similar to the infusion catheter 10 illustrated in FIG. 1. For example, the infusion catheter 110 may include an elongate catheter shaft 12 extending distally from a hub assembly 20, having a proximal end 16 attached to the hub assembly 20 and a distal end 18 opposite the proximal end 16. The catheter shaft 12 may be a dual lumen catheter shaft having a first, infusion fluid lumen 34 and a second, guidewire lumen 36 extending along at least a portion of the catheter shaft 12 configured for advancing the infusion catheter 110 over the guidewire 30.

The catheter shaft 12 may include an outer tubular member 13 and an inner tubular member 14 extending through the lumen of the outer tubular member 13. With the SOE catheter construction of FIG. 3, the infusion fluid lumen 34 may be defined by the outer tubular member 13 through the proximal portion of the catheter shaft 12, while the infusion fluid lumen 34 may be defined between an outer surface of the inner tubular member 14 and an inner surface of the outer tubular member 13 through the distal portion of the catheter shaft 12. In embodiments in which the catheter is an OTW construction, the infusion fluid lumen 34 may be defined between an outer surface of the inner tubular member 14 and an inner surface of the outer tubular member 13 throughout the catheter shaft 12. The hub assembly 20 may include a proximal port 22 in fluid communication with the infusion fluid lumen 34. A source of infusion fluid (not shown), such as an infusion pump, syringe, etc., may be coupled to the proximal port 22 to supply infusion fluid to the infusion fluid lumen 34.

The lumen of the inner tubular member 14 may define the guidewire lumen 36 with a distal guidewire port 28 proximate the distal end of the inner tubular member 14 and a proximal guidewire port 26 proximate the proximal end of the inner tubular member 14.

The catheter 110 may include an inflatable balloon 120 mounted on a distal region of the catheter shaft 12. For example, the inflatable balloon 120 may include a proximal balloon waist secured (e.g., thermally or adhesively bonded) to a distal end of the outer tubular member 13 and a distal balloon waist secured (e.g., thermally or adhesively bonded) to a distal end of the inner tubular member 14. The infusion fluid lumen 34 extending along the catheter shaft 12 may be in fluid communication with the interior of the inflatable balloon 120 to delivery infusion fluid to the inflatable balloon 120.

The inflatable balloon 120 may include one or more fluid infusion openings 140 (e.g., holes, apertures) configured to permit infusion fluid to exit the balloon 120 from the infusion fluid lumen 34. For example, the balloon 120 may include a plurality of fluid infusion openings 140 extending through a wall of the balloon 120 when the balloon 120 is inflated with the infusion fluid. In one illustrative embodiment, the balloon 120 may include four fluid infusion openings 140 equidistantly spaced circumferentially around the balloon 120 (i.e., with each fluid infusion opening 140 arranged about 90° from another fluid infusion opening 140). In other embodiments, the balloon 120 may include one, two, three, or more fluid infusion openings 140 arranged around the perimeter of the balloon 120.

The fluid infusion openings 140 may be configured to expel an infusion fluid radially outward from the balloon 120 to facilitate mixing of the infusion fluid with blood flowing through the vessel lumen. For example, the fluid infusion openings 140 may be located on the distal cone portion of the balloon 120, on a cylindrical body portion of the balloon 120, or at a different position, if desired. In some instances, the balloon may be configured to create turbulence in the blood flow to facilitate mixing the infusion fluid with the blood flowing distal of the balloon 120.

The fluid infusion openings 140 may be configured to generate a jet of infusion fluid exiting the balloon 120. For example, the fluid infusion openings 140 may be appropriately sized to generate a pressure stream of the infusion fluid exiting the fluid infusion openings 140. The size of the fluid infusion openings 140 may be selected based on the volume of infusion fluid to ensure a jet of infusion fluid is formed exiting the balloon 120.

Similar to the infusion catheter 10, the catheter shaft 12 of the infusion catheter 110 may also include one or more fluid holes 50 (e.g., openings, apertures) located at the distal end region of the catheter 110 configured to permit infusion fluid to pass from the infusion fluid lumen 34 into the guidewire lumen 36. For example, the catheter shaft 12 may include one or more fluid holes 50 extending through a wall of the inner tubular member 14 from an outer surface of the inner tubular member 14 to an inner surface of the inner tubular member 14. The fluid hole(s) 50 may be a weeping hole configured to allow infusion fluid to weep or exude slowly into the guidewire lumen 36 from the infusion fluid lumen 34. For instance, the fluid hole(s) 50 may be configured to allow infusion fluid to weep, drip, trickle, ooze or otherwise slowly exude into the guidewire lumen 36.

Figure 4:
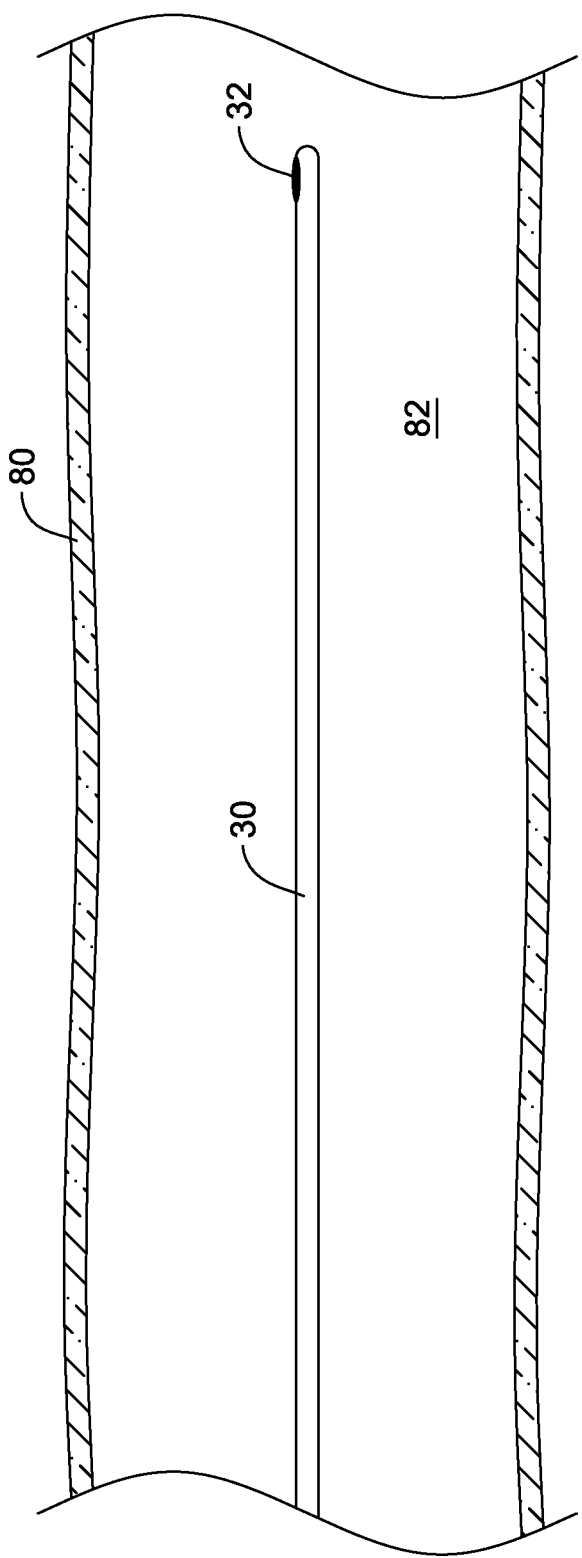
FIGS. 4-7 illustrate aspects of an exemplary method of determining blood flow through a body vessel using the catheter system of FIG. 1.

FIGS. 4-7 illustrate aspects of an exemplary method of determining blood flow through a body vessel using the catheter system of FIG. 1. As shown in FIG. 4, a guidewire, such as the guidewire 30 having a temperature sensor 32 mounted on a distal end region thereof, may be advanced through a lumen 82 of a blood vessel 80 of the vasculature to a desired target location, such as in a coronary artery, for example.

Figure 5:
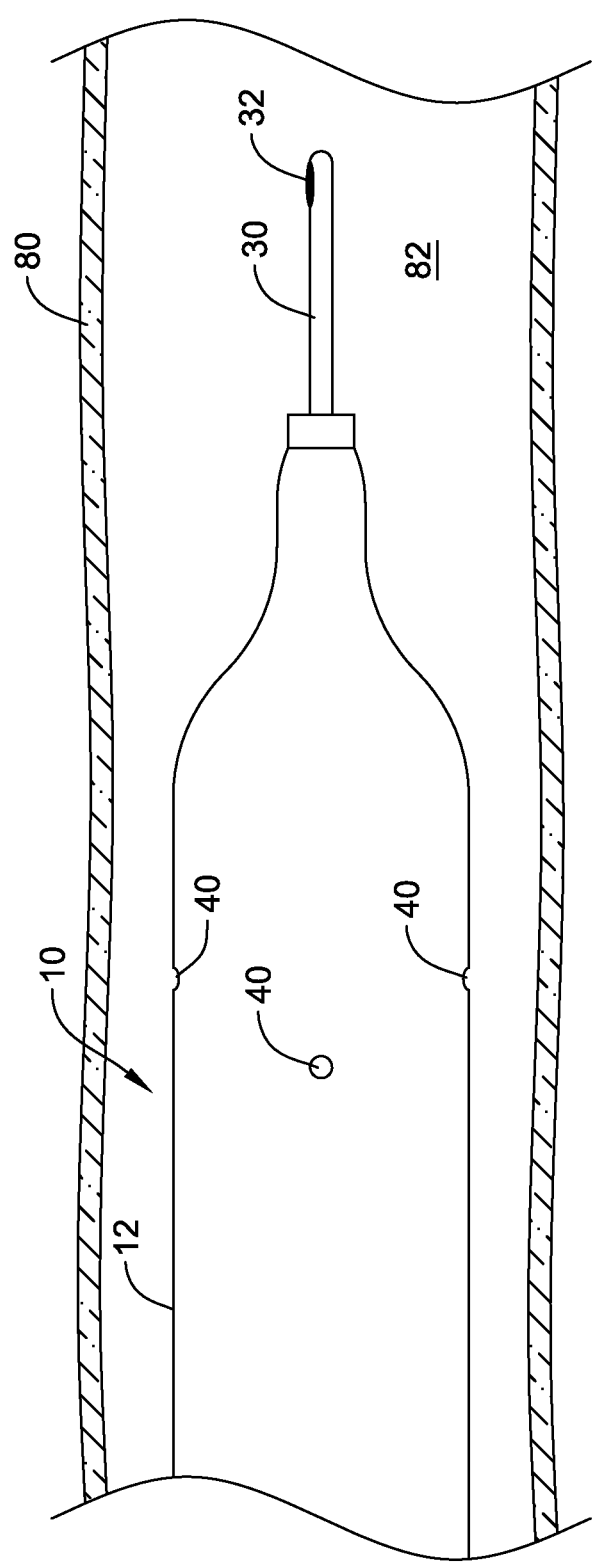

The infusion catheter 10 may then be advanced over the guidewire 30 to the target location within the blood vessel 80, as shown in FIG. 5. In other embodiments, the infusion catheter 10 may be advanced over a different guidewire, such as a conventional guidewire, to the target location, and subsequently the guidewire may be exchanged for the guidewire 30 having a temperature sensor 32 mounted thereon.

With the temperature sensor 32 positioned distal of the infusion catheter 10 the actual temperature $T_b$ of the blood may be measured with the temperature sensor 32 and recorded. In other instances, an estimated temperature (e.g., 98.6° F.) may be used as the temperature $T_b$ of the blood for subsequent calculations.

Figure 6:
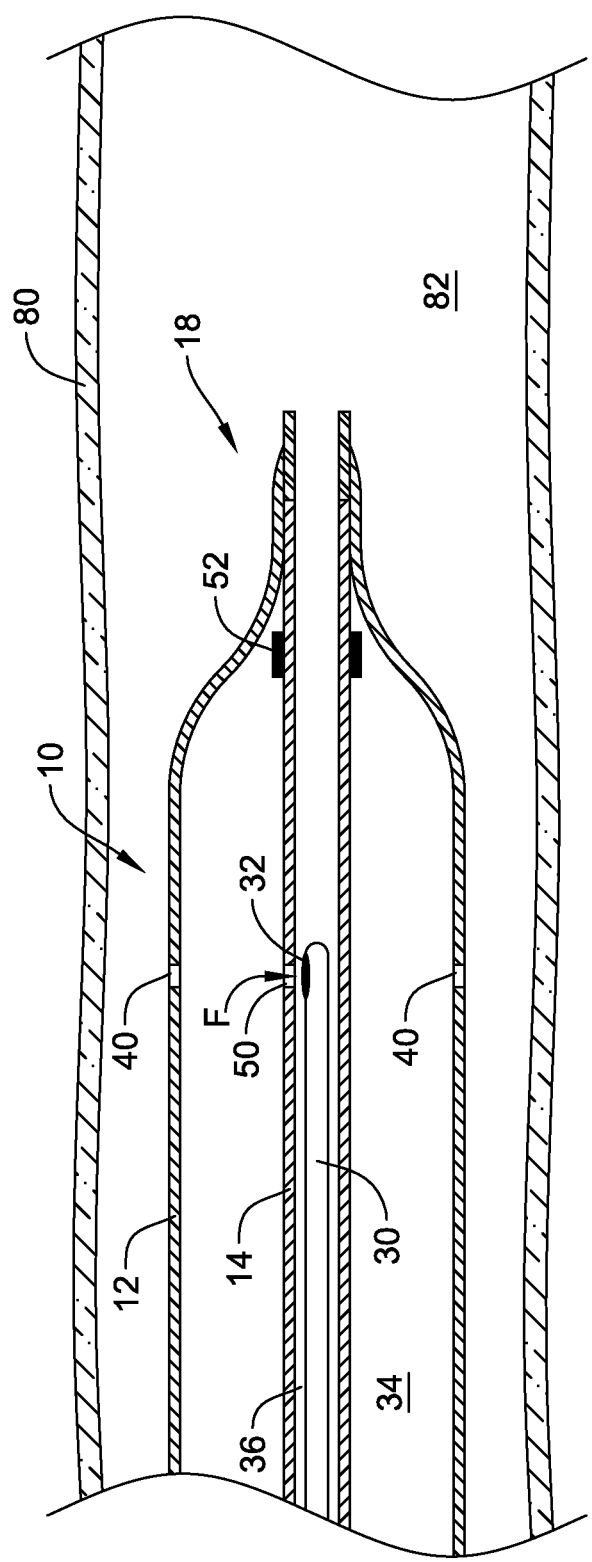

The guidewire 30 may be withdrawn proximally to reposition the sensor 32 inside the guidewire lumen 36, as shown in FIG. 6. For example, the sensor 32 may be positioned within the guidewire lumen 36 adjacent to the fluid hole 50 extending through the inner tubular member 14. The infusion fluid F (e.g., saline) may be delivered through the infusion fluid lumen 34 to the distal end region of the catheter 10. For example, the infusion fluid F may be provided to the distal region of the catheter 10 at a pressure of about 1 ATM to about 30 ATM. A small amount of the infusion fluid F may enter the guidewire lumen 36 through the fluid hole(s) 50 from the infusion fluid lumen 34. Accordingly, with the temperature sensor 32 positioned in the guidewire lumen 36, the actual temperature $T_f$ of the infusion fluid F at the distal end region of the catheter 10 may be measured and recorded. For example, the temperature sensor 32 may be positioned adjacent to the fluid hole(s) 50 such that infusion fluid F passing into the guidewire lumen 36 may come into direct contact with the temperature sensor 32 in the guidewire lumen 36. In other instances, the temperature sensor 32 may be otherwise positioned within the guidewire lumen 36 such that infusion fluid F located in the guidewire lumen 36 may come into direct contact with the temperature sensor 32 in the guidewire lumen 36.

Figure 7:
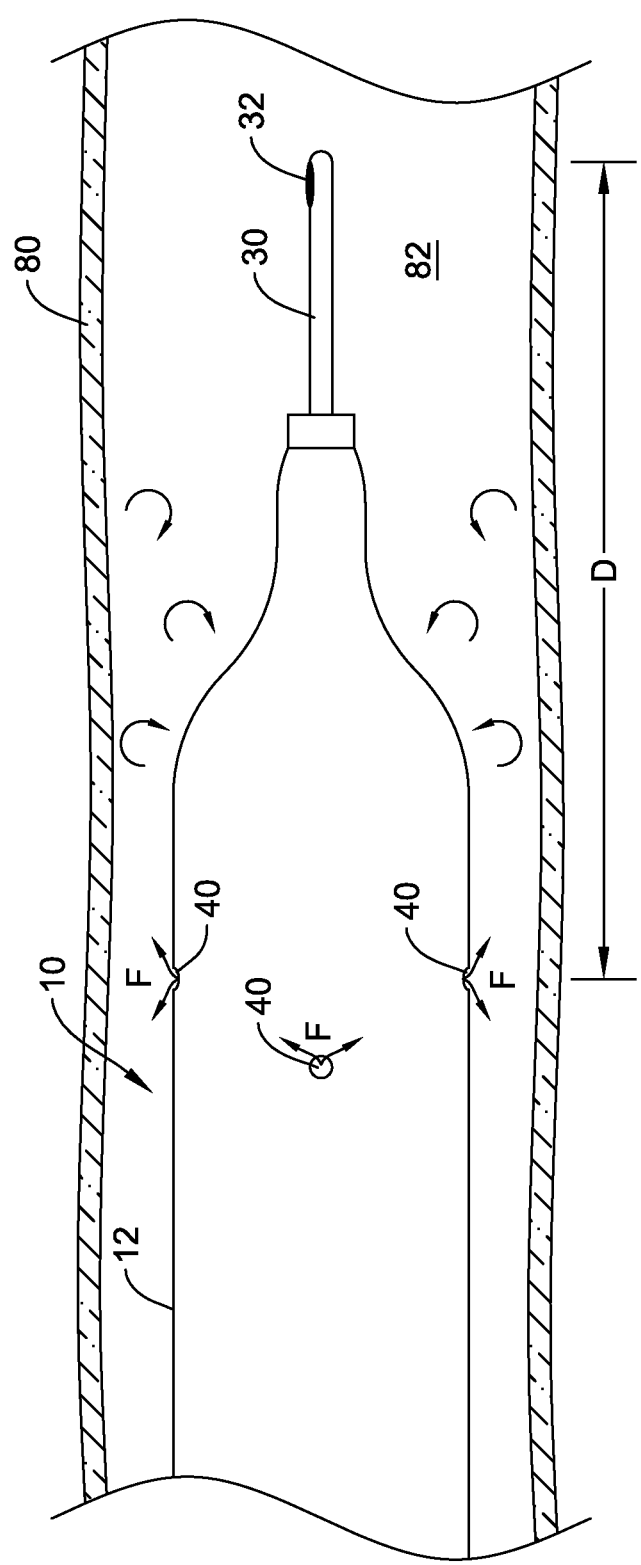

The temperature sensor 32 on the guidewire 30 may then be advanced to a location distal of the catheter 10, as shown in FIG. 7. For example, the temperature sensor 32 may be advanced distally to a position located a distance D from the fluid infusion openings 40. In some instances, the distance D may be about 3 centimeters or more, about 4 centimeters or more, about 5 centimeters or more, or about 6 centimeters or more to ensure the infusion fluid F completely mixes with the blood prior to reaching the temperature sensor 32. For example, the temperature sensor 32 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 40 on the catheter shaft 12.

The infusion fluid F may be infused into the blood stream in the lumen 82 of the blood vessel 80 through the fluid infusion openings 40 from the infusion fluid lumen 34. For example, a continuous flow of infusion fluid F at a known flow rate through the infusion fluid lumen 34 may be provided with an infusion pump, with a substantial portion of the infusion fluid F exiting the catheter 10 through the infusion fluid lumen(s) 40 and a small amount of the infusion fluid F exiting the catheter 10 via the guidewire lumen 36. The flow rate of the infusion fluid F may be set to any desired flow rate, for example, a continuous flow rate of about 15 ml/min, about 20 ml/min, about 25 ml/min, about 30 ml/min, about 35 ml/min, or about 40 ml/min. The infusion fluid F may mix with the blood flowing through the blood vessel 80 to provide a mixture of blood and infusion fluid F. If the temperature $T_f$ of the infusion fluid F (e.g., at room temperature) is less than the temperature $T_b$ of the blood, then the mixture of blood and infusion fluid F may have a temperature $T_m$ less than the temperature $T_b$ of the blood.

With the temperature sensor 32 positioned a distance D distal of the infusion fluid opening(s) 40, the temperature $T_m$ of the mixture of blood and infusion fluid F may be measured with the temperature sensor 32 and recorded.

Multiple temperature measurements of the infusion fluid, blood and/or the mixture of blood and infusion fluid may be taken to calculate an average, or adjusted temperature for calculating the blood flow rate through the blood vessel 80.

It is noted that in some instances the temperatures may be measured in any desired order. For example, the temperature $T_m$ of the mixture of the infusion fluid and the blood may be measured first with the temperature sensor 32 located a distance D distal of the catheter 10 as shown in FIG. 7, and then the temperature $T_f$ of the infusion fluid entering the guidewire lumen 36 may be measured by withdrawing the temperature sensor 32 into the guidewire lumen 36 as shown in FIG. 6.

Although a single temperature sensor 32 is illustrated for measuring the temperature $T_f$ of the fluid F, the temperature $T_b$ of the blood, and the temperature $T_m$ of the mixture of blood and infusion fluid, in some instances, the temperature $T_f$ of the fluid F, the temperature $T_b$ of the blood, and/or the temperature $T_m$ of the mixture of blood and infusion fluid may be measured using a different temperature sensor positioned on the guidewire 30 distinct from the temperature sensor 32, a temperature sensor positioned on a second guidewire, positioned on the catheter 10, or otherwise positioned to take the corresponding temperature.

It is noted that the patient with normally be brought to a state of hyperemia, prior to taking the temperature measurements. The measured temperatures may then be used to calculate the actual, absolute blood flow rate of blood in the blood vessel 80 at the target location. For instance, the blood flow rate, which is based on the measured temperature $T_b$ of the blood and the measured temperature $T_m$ of the mixture of the fluid and the blood, may be calculated using the following equation:

$$Q_b = Q_f \times (T_f - T_b)/(T_m - T_b)$$

Where:
$Q_b$=the actual blood flow rate
$Q_f$=the flow rate of the infusion fluid
$T_f$=the temperature of the infusion fluid
$T_b$=the temperature of the blood
$T_m$=the temperature of the mixture of blood and infusion fluid Accordingly, the actual, absolute flow rate of the blood through the blood vessel 80 at the target location may be calculated. The absolute blood flow rate may be used in a diagnostic evaluation for determining a medical condition of the patient. Furthermore, the calculated absolute blood flow rate could be combined with other measurements to provide further diagnostic analysis. For example, the calculated absolute blood flow rate may be combined with an absolute blood pressure measured at the target location in the blood vessel 80 to determine the absolute resistance of the blood vessel 80.

In some instances, the fractional flow reserve (FFR) may be used to measure the pressure drop across a stenosis or narrowing in the blood vessel 80. Fractional flow reserve (FFR) may be calculated with the following equation:

$$FFR = P_d/P_p$$

Where:
$P_d$=measured pressure distal of the stenosis
$P_p$=measured pressure proximal of the stenosis Having calculated the FFR based on the measured pressures proximal and distal to the stenosis or narrowing, and the absolute flow rate of the blood through the blood vessel proximate the stenosis or narrowing, one can calculate the normal maximum flow rate through the blood vessel with the following equation:

$$FFR = Q_b/Q_n$$

Where:
$Q_b$=the actual blood flow rate
$Q_n$=the normal maximum flow rate

When the flow rate of the blood has been calculated and the pressures proximal and distal of the stenosis have been calculated, the resistance of the stenosis or narrowing of the blood vessel 80 can be calculated with the following equation:

$$R_s = (P_p - P_d)/Q_b$$

Where:
$R_s$=resistance across the stenosis or narrowing
$P_d$=measured pressure distal of the stenosis or narrowing
$P_p$=measured pressure proximal of the stenosis or narrowing
$Q_b$=the actual blood flow rate Thus, the measured actual blood flow rate, as well as other calculated parameters, may be useful for the diagnosis and understanding of a number of pathophysiological conditions such as heart transplantation, stem cell therapy, or a transmural myocardial infarction, for example.

Figure 8:
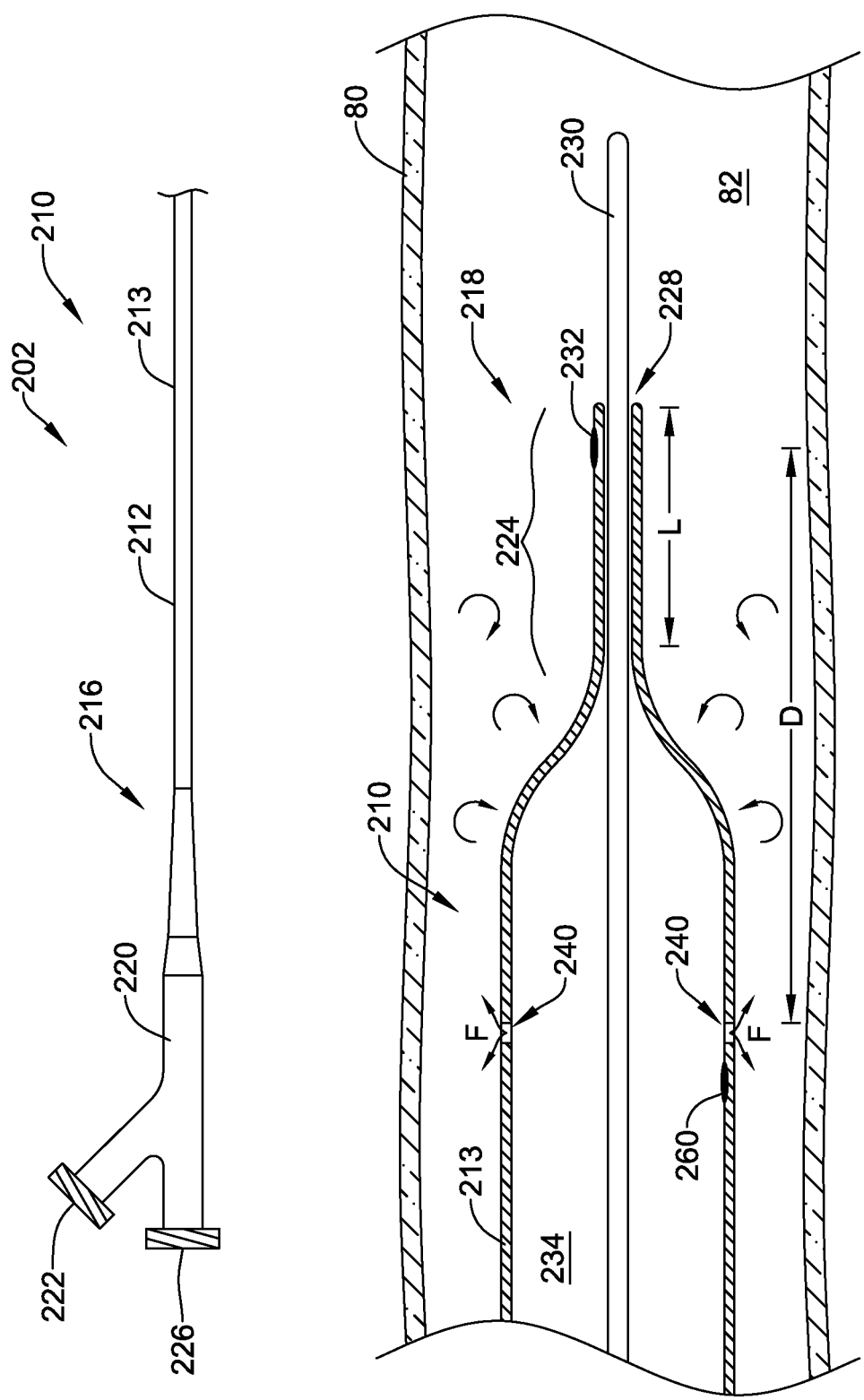
FIG. 8 is a schematic representation of another embodiment of a catheter system for determining blood flow through a body vessel using a thermodilution technique.

Another embodiment of a catheter system 202 for determining blood flow through a body vessel using a thermodilution technique is illustrated in FIG. 8. The catheter system 202 may include an infusion catheter 210, and in some instances an associated guidewire 30. The infusion catheter 210 may include an elongate catheter shaft 212 extending distally from a hub assembly 220. The catheter shaft 212 may have a proximal end 216 attached to the hub assembly 220 and a distal end 218 opposite the proximal end 216. The catheter shaft 212 may be a single lumen catheter shaft formed of a tubular member 213 having an infusion fluid lumen 234 defined therein.

The catheter shaft 212 may include a reduced diameter distal end region 224 extending to the distal end 218 of the catheter shaft 212. A guidewire 230 may extend through the infusion fluid lumen 234 of the catheter shaft 212 from a proximal guidewire port 226 located in the hub assembly 220 to a distal guidewire port 228 at the distal tip of the reduced diameter distal end region 224. The inner diameter of the reduced diameter distal end region 224 may be closely sized to the diameter of the guidewire 230 such that substantially no infusion fluid leaks out of the catheter shaft 212 through the distal guidewire port 228. The reduced diameter distal end region 224 may have a length L of about 3 centimeters to about 6 centimeters, for example.

The hub assembly 220 may also include a proximal fluid port 222 in fluid communication with the infusion fluid lumen 234. A source of infusion fluid (not shown), such as an infusion pump, syringe, etc., may be coupled to the proximal fluid port 222 to supply infusion fluid F to the infusion fluid lumen 234.

The catheter shaft 212 may include one or more fluid infusion openings 240 (e.g., holes, apertures) located at a distal end region of the catheter 210. The fluid infusion openings 240 may be in fluid communication with the infusion fluid lumen 234 and may be configured to permit infusion fluid to exit the catheter 210 from the infusion fluid lumen 234 proximate the distal end 218 of the catheter shaft 212. For example, the catheter shaft 212 may include a plurality of fluid infusion openings 240 extending through a wall of the tubular member 213 from an inner surface of the tubular member 213 to an outer surface of the tubular member 213. The infusion openings 240 may be of a similar construction and arrangement as the infusion openings 40 of the catheter 10 described above.

The fluid infusion openings 240 may be configured to expel an infusion fluid in a radially outward direction from each of the fluid infusion openings 240 to facilitate mixing of the infusion fluid with blood flowing through the vessel lumen. In other embodiments, the fluid infusion openings 240 may be arranged in a different orientation, such as in a fashion to permit infusion fluid to be expelled generally distally from the catheter shaft 212, if desired.

The infusion catheter 210 may include a first temperature sensor 260, such as a thermistor or a thermocouple, positioned within the infusion fluid lumen 234 of the catheter shaft 212 proximate the fluid infusion openings 240. The temperature sensor 260 may be configured to be in direct contact with the infusion fluid F within the infusion fluid lumen 234 to measure the temperature $T_f$ of the infusion fluid F exiting the infusion fluid lumen 234 through the fluid infusion openings 240.

The infusion catheter 210 may also include a second temperature sensor 232, such as a thermistor or a thermocouple, positioned on an exterior of the elongated reduced diameter distal end region 224 proximate the distal end 218 of the catheter shaft 212. The second temperature sensor 232 may be positioned a distance D distal of the one or more fluid infusion openings 240. The second temperature sensor 232, mounted on the exterior of the catheter shaft 212, may be used to measure the temperature $T_b$ of the blood flowing in the lumen 82 of the blood vessel 80, as well as the temperature $T_m$ of the mixture of blood and infusion fluid flowing distal of the infusion fluid openings 240. In some instances, the distance D may be about 3 centimeters or more, about 4 centimeters or more, about 5 centimeters or more, or about 6 centimeters or more to ensure the infusion fluid F completely mixes with the blood prior to reaching the temperature sensor 232. For example, the temperature sensor 232 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 240 on the catheter shaft 212.

The measured temperatures obtained with the infusion catheter 210 may then be used to calculate the actual, absolute blood flow rate of blood in the blood vessel 80 at the target location, as well as other calculated parameters, which may be useful for the diagnosis and understanding of a number of pathophysiological conditions.

Figure 9:
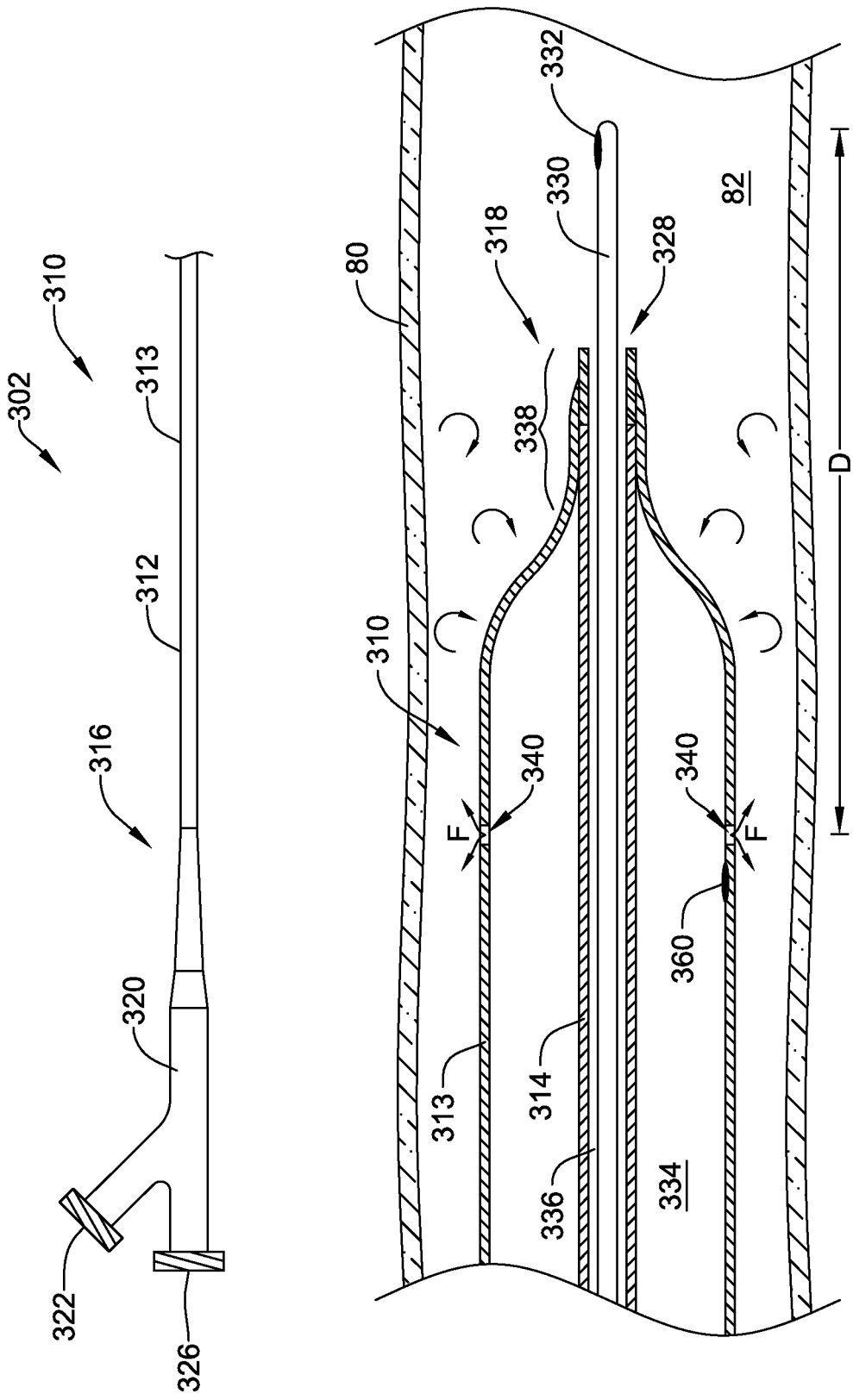
FIG. 9 is a schematic representation of another embodiment of a catheter system for determining blood flow through a body vessel using a thermodilution technique.

Another embodiment of a catheter system 302 for determining blood flow through a body vessel using a thermodilution technique is illustrated in FIG. 9. The catheter system 302 may include an infusion catheter 310, and in some instances an associated guidewire 330. The infusion catheter 310 may include an elongate catheter shaft 312 extending distally from a hub assembly 320. The catheter shaft 312 may have a proximal end 316 attached to the hub assembly 320 and a distal end 318 opposite the proximal end 316. The catheter shaft 312 may be a dual lumen catheter shaft having an infusion fluid lumen 334 and a guidewire lumen 336 extending through the catheter shaft 212 configured for advancing the infusion catheter 310 over a guidewire 330. As shown in FIG. 9, the catheter 310 may be an over-the-wire (OTW) catheter in which the guidewire lumen 336 may extend through the entire length of the catheter shaft 312 from a proximal guidewire port 326 located in the hub assembly 320 to a distal guidewire port 328 at the distal end 218 of the catheter shaft 312. However, in other embodiments, the catheter 310 may be a single-operator-exchange (SOE) catheter in which the guidewire lumen 336 extends only through a distal portion of the catheter shaft 312.

The catheter shaft 312 may include an outer tubular member 313 and an inner tubular member 314 extending through the lumen of the outer tubular member 313. In some instances, the outer tubular member 313 may coaxially surround the inner tubular member 314. The lumen of the inner tubular member 314 may define the guidewire lumen 336. The infusion fluid lumen 334 may be defined between an outer surface of the inner tubular member 314 and an inner surface of the outer tubular member 313. The hub assembly 320 may include a proximal port 322 in fluid communication with the infusion fluid lumen 334. A source of infusion fluid (not shown), such as an infusion pump, syringe, etc., may be coupled to the proximal port 322 to supply infusion fluid to the infusion fluid lumen 334.

A distal end portion 338 of the outer tubular member 313 may be a reduced diameter portion or necked portion, secured to the inner tubular member 314 to seal the infusion fluid lumen 334 proximate the distal end 318 of the catheter shaft 312. For example, the distal end portion 338 may include a tapered region in which the outer tubular member 313 tapers down to a reduced inner and/or outer diameter at the distal end of the outer tubular member 313. Thus, the inner surface of a distal end portion of the outer tubular member 313 may be secured to the outer surface of a distal end portion of the inner tubular member 314 in the distal end portion 38. The outer tubular member 313 may be secured to the inner tubular member 314, for example, by laser welding, hot jaws, or other thermal bonding method, an adhesive bonding method, or other bonding method if desired.

In some instances, the catheter shaft 312 may include a distal tip, formed as a separate component and secured at the distal end 318 of the catheter shaft 312, or the distal tip may be formed as a unitary portion of the inner tubular member 314 and/or the outer tubular member 313.

The catheter shaft 312 may include one or more fluid infusion openings 340 (e.g., holes, apertures) located at a distal end region of the catheter 310. The fluid infusion openings 340 may be in fluid communication with the infusion fluid lumen 334 and may be configured to permit infusion fluid to exit the catheter 310 from the infusion fluid lumen 334 proximate the distal end 318 of the catheter shaft 312. For example, the catheter shaft 312 may include a plurality of fluid infusion openings 340 extending through a wall of the outer tubular member 313 from an inner surface of the outer tubular member 313 to an outer surface of the outer tubular member 313. The infusion fluid openings 340 may be of a similar construction and arrangement as the infusion openings 40 of the catheter 10 described above.

The fluid infusion openings 340 may be configured to expel an infusion fluid F in a radially outward direction from each of the fluid infusion openings 340 to facilitate mixing of the infusion fluid F with blood flowing through the vessel lumen. In other embodiments, the fluid infusion openings 340 may be arranged in a different orientation, such as in a fashion to permit infusion fluid to be expelled generally distally from the catheter shaft 312, if desired.

The infusion catheter 310 may include a temperature sensor 360, such as a thermistor or a thermocouple, positioned within the infusion fluid lumen 334 of the catheter shaft 312 proximate the fluid infusion openings 340. For example, the temperature sensor 360 may be secured to the inner surface of the outer tubular member 313 proximate one of the fluid infusion openings 340. The temperature sensor 360 may be configured to be in direct contact with the infusion fluid F within the infusion fluid lumen 334 to measure the temperature $T_f$ of the infusion fluid F exiting the infusion fluid lumen 334 through the fluid infusion openings 340.

The catheter system 302 may also include a guidewire 330 sized and configured to be disposed through the guidewire lumen 336 of the infusion catheter 310 such that the infusion catheter 310 may be advanced along the guidewire 330 to a target location in the vasculature. The guidewire 330 may include a temperature sensor 332, such as a thermistor or a thermocouple, mounted on a distal end region of the guidewire 330. One illustrative embodiment of a guidewire 330 having a temperature sensor 332 mounted thereon is described in U.S. Pat. No. 6,343,514, which is incorporated by reference herein. In some instances, the guidewire 330 may also include a pressure sensor located at the distal end region of the guidewire 330 for measuring blood pressure at a target location within the vasculature. The temperature sensor 332, mounted on the guidewire 330, may be used to measure the temperature $T_b$ of the blood flowing in the lumen 82 of the blood vessel 80, as well as the temperature $T_m$ of the mixture of blood and infusion fluid flowing distal of the infusion fluid openings 340. The temperature sensor 332 may be positioned a distance D distal of the infusion fluid openings 340 when taking temperature measurements of the mixture of blood and infusion fluid. In some instances, the distance D may be about 3 centimeters or more, about 4 centimeters or more, about 5 centimeters or more, or about 6 centimeters or more to ensure the infusion fluid F completely mixes with the blood prior to reaching the temperature sensor 332. For example, the temperature sensor 332 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 340 on the catheter shaft 312.

The measured temperatures obtained with the infusion catheter 310 and the guidewire 330 may then be used to calculate the actual, absolute blood flow rate of blood in the blood vessel 80 at the target location, as well as other calculated parameters, which may be useful for the diagnosis and understanding of a number of pathophysiological conditions.

Figure 10:
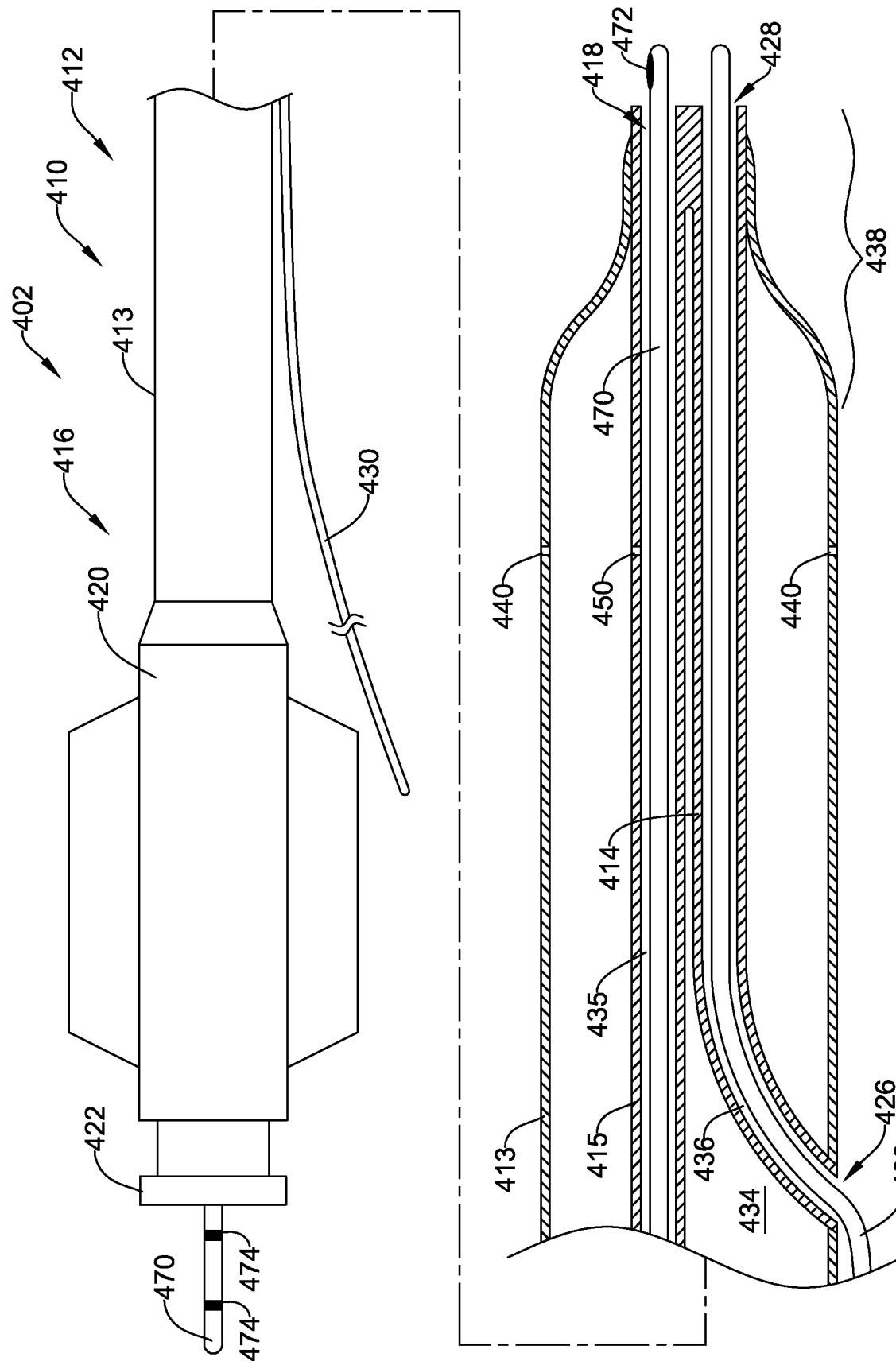
FIG. 10 is a schematic representation of another embodiment of a catheter system for determining blood flow through a body vessel using a thermodilution technique.

Another embodiment of a catheter system 402 for determining blood flow through a body vessel using a thermodilution technique is illustrated in FIG. 10. The catheter system 402 may include an infusion catheter 410, and in some instances an associated temperature probe 470 and/or guidewire 430. In many respects the infusion catheter 410 may be similar to the infusion catheter 10 illustrated in FIG. 1. For example, the infusion catheter 410 may include an elongate catheter shaft 412 extending distally from a hub assembly 420, having a proximal end 416 attached to the hub assembly 420 and a distal end 418 opposite the proximal end 416. The catheter shaft 412 may be a triple lumen catheter shaft having a first, infusion fluid lumen 434 and a second, an auxiliary lumen 435 (e.g., a temperature probe lumen), and a third, guidewire lumen 436 extending along at least a portion of the catheter shaft 412 configured for advancing the infusion catheter 410 over the guidewire 430.

The catheter shaft 412 may include an outer tubular member 413 and first and second inner tubular members 415, 414 extending through the lumen of the outer tubular member 413. The infusion fluid lumen 434 may be defined by the portion of the lumen of the outer tubular member 413 exterior of the first and second inner tubular members 415, 414. The hub assembly 420 may include a proximal port 422 in fluid communication with the infusion fluid lumen 434. A source of infusion fluid (not shown), such as an infusion pump, syringe, etc., may be coupled to the proximal port 422 to supply infusion fluid to the infusion fluid lumen 434. In other embodiments, the catheter shaft 412 may be an extruded tubular member including three lumens extending therethrough, for example.

The lumen of the second inner tubular member 414 may define the guidewire lumen 436 with a distal guidewire port 428 proximate the distal end of the second inner tubular member 414 and a proximal guidewire port 426 proximate the proximal end of the second inner tubular member 414. The guidewire 430 may be extendable through the guidewire lumen 436.

The lumen of the first inner tubular member 415 may define the auxiliary lumen 435 configured for longitudinally receiving an elongate member, such as a temperature probe 470 therethrough. The auxiliary lumen 435 may extend from the proximal end of the catheter 410 to the distal end of the catheter 410, with a proximal portion of the temperature probe 470 extending proximal of the auxiliary lumen 435 (e.g., proximal of the catheter 410) and a distal portion of the temperature probe 470 extending distal of the auxiliary lumen 435 (e.g., distal of the catheter 410).

A distal end portion 438 of the outer tubular member 413 may be a reduced diameter portion or necked portion, secured to the first inner tubular member 415 and/or the second inner tubular member 414 to seal the infusion lumen 434 proximate the distal end 418 of the catheter shaft 412. For example, the distal end portion 438 may include a tapered region in which the outer tubular member 413 tapers down to a reduced inner and/or outer diameter at the distal end of the outer tubular member 413. Thus, the inner surface of a distal end portion of the outer tubular member 413 may be secured to the outer surface of a distal end portion of the first inner tubular member 415 and/or the outer surface of a distal end portion of the second inner tubular member 414 in the distal end portion 438. The outer tubular member 413 may be secured to the inner tubular members 414, 415, for example, by laser welding, hot jaws, or other thermal bonding method, an adhesive bonding method, or other bonding method if desired.

The catheter shaft 412 may include one or more fluid infusion openings 440 (e.g., holes, apertures) located at a distal end region of the catheter 410. The fluid infusion openings 440 may be in fluid communication with the infusion fluid lumen 434 and may be configured to permit infusion fluid to exit the catheter 410 from the infusion fluid lumen 434 proximate the distal end 418 of the catheter shaft 412. For example, the catheter shaft 412 may include a plurality of fluid infusion openings 440 extending through a wall of the outer tubular member 413 from an inner surface of the outer tubular member 413 to an outer surface of the outer tubular member 413. The infusion fluid openings 440 may be of a similar construction and arrangement as the infusion openings 40 of the catheter 10 described above.

The fluid infusion openings 440 may be configured to expel an infusion fluid F in a radially outward direction from each of the fluid infusion openings 440 to facilitate mixing of the infusion fluid F with blood flowing through the vessel lumen. In other embodiments, the fluid infusion openings 440 may be arranged in a different orientation, such as in a fashion to permit infusion fluid to be expelled generally distally from the catheter shaft 412, if desired.

The catheter shaft 412 may also include one or more fluid holes 450 (e.g., openings, apertures) located at the distal end region of the catheter 410. The fluid hole(s) may be in fluid communication with the infusion fluid lumen 434 and may be configured to permit infusion fluid to pass from the infusion fluid lumen 434 into the auxiliary lumen 435. For example, the catheter shaft 412 may include one or more fluid holes 450 extending through a wall of the first inner tubular member 415 from an outer surface of the first inner tubular member 415 to an inner surface of the first inner tubular member 415. The catheter shaft 412 may include one fluid hole 450 extending through the wall of the first inner tubular member 415 to permit infusion fluid F to enter the auxiliary lumen 435 from the infusion fluid lumen 434, or the catheter shaft 412 may include two, three or more such fluid holes 450, if desired.

The fluid hole(s) 450 may be a weeping hole configured to allow infusion fluid to weep or exude slowly into the auxiliary lumen 435 from the infusion fluid lumen 434. For instance, the fluid hole(s) 450 may be configured to allow infusion fluid to weep, drip, trickle, ooze or otherwise slowly exude into the auxiliary lumen 435. In some instances, the fluid hole(s) 450 may have a diameter of about 100 microns (0.100 millimeters) to about 300 microns (0.300 millimeters), about 100 microns (0.100 millimeters) to about 200 microns (0.200 millimeters), or about 200 microns (0.200 millimeters) to about 300 microns (0.300 millimeters), for example.

The catheter system 402 may also include a temperature probe 470 sized and configured to be disposed through the auxiliary lumen 435 of the infusion catheter 410. The temperature probe 470 may be longitudinally actuatable through the auxiliary lumen 435 relative to the catheter 410. The temperature probe 470 may include a temperature sensor 472, such as a thermistor or a thermocouple, mounted on a distal end region of the temperature probe 470. One illustrative embodiment of a temperature probe 470 is a fiber optic temperature sensor available from Neoptix. The temperature sensor 472, mounted on the temperature probe 470, may be used to measure the temperature $T_b$ of the blood flowing in the lumen of the blood vessel, as well as the temperature $T_m$ of the mixture of blood and infusion fluid flowing distal of the infusion fluid openings 440. The temperature sensor 472 may be positioned a distance distal of the infusion fluid openings 440 when taking temperature measurements of the mixture of blood and infusion fluid. In some instances, the distance may be about 3 centimeters or more, about 4 centimeters or more, about 5 centimeters or more, or about 6 centimeters or more to ensure the infusion fluid F completely mixes with the blood prior to reaching the temperature sensor 472. For example, the temperature sensor 472 may be positioned a distance D of about 3 centimeters to about 8 centimeters, about 3 centimeters to about 6 centimeters, about 4 centimeters to about 8 centimeters, or about 4 centimeters to about 6 centimeters distal of the infusion fluid openings 440 on the catheter shaft 412.

The temperature probe 470 may be longitudinally actuated relative to the catheter 410 to position the sensor 472 inside the auxiliary lumen 435 to obtain a measurement of the temperature $T_f$ of the infusion fluid. For example, the sensor 472 may be positioned within the auxiliary lumen 435 adjacent to the fluid hole 450 extending through the first inner tubular member 415. The infusion fluid F (e.g., saline) may be delivered through the infusion fluid lumen 434 to the distal end region of the catheter 410. For example, the infusion fluid F may be provided to the distal region of the catheter 410 at a pressure of about 1 ATM to about 30 ATM. A small amount of the infusion fluid F may enter the auxiliary lumen 435 through the fluid hole(s) 450 from the infusion fluid lumen 434. Accordingly, with the temperature sensor 472 positioned in the auxiliary lumen 435, the actual temperature $T_f$ of the infusion fluid F at the distal end region of the catheter 410 may be measured and recorded. For example, the temperature sensor 472 may be positioned adjacent to the fluid hole(s) 450 such that infusion fluid F passing into the auxiliary lumen 435 may come into direct contact with the temperature sensor 472 in the auxiliary lumen 435. In other instances, the temperature sensor 472 may be otherwise positioned within the auxiliary lumen 435 such that infusion fluid F located in the auxiliary lumen 435 may come into direct contact with the temperature sensor 472 in the auxiliary lumen 435.

The temperature probe 470 may include a visual marker system including markings or indicia 474 on a proximal portion of the temperature probe 470 that medical personnel may use to determine the position of the temperature sensor 472 relative to the fluid infusion opening(s) 440 and/or the fluid hole(s) 450. The markings or indicia 474 may be located on the temperature probe 470 proximal of the hub assembly 420 for direct observation by an operator. In some instances, the temperature probe 470 may include a first mark or indicia 474 at a known location corresponding to when the temperature sensor 472 is positioned proximate the fluid hole 450, a second mark or indicia 474 at a known location corresponding to when the temperature sensor 472 is located a first known distance (e.g., 3 centimeters) distal of the catheter 410 and thus the fluid infusion openings 440, a third mark or indicia 474 at a known location corresponding to when the temperature sensor 472 is at a second distance (e.g., 4 centimeters) distal of the catheter 410 and thus the fluid infusion openings 440, a fourth mark or indicia 474 at a known location corresponding to when the temperature sensor 472 is at a third distance (e.g., 5 centimeters) distal of the catheter 410 and thus the fluid infusion openings 440, a fifth mark or indicia 474 at a known location corresponding to when the temperature sensor 472 is at a fourth distance (e.g., 6 centimeters) distal of the catheter 410 and thus the fluid infusion openings 440, etc.

The measured temperatures obtained with the temperature probe 470 may then be used to calculate the actual, absolute blood flow rate of blood in a blood vessel at the target location, as well as other calculated parameters, which may be useful for the diagnosis and understanding of a number of pathophysiological conditions.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A catheter system for determining blood flow in a body lumen, the system comprising:
    a catheter including:
        an outer tubular member;
        an inner tubular member disposed within the outer tubular member;
        wherein an inner wall surface of the outer tubular member is attached to an outer wall surface of the inner tubular member at a position adjacent to a distal end region of the catheter;
        a first, fluid lumen, at least a portion thereof defined between the inner tubular member and the outer tubular member;
        a second lumen defined by the inner tubular member, the second lumen having an open distal end such that the catheter is configured to be advanced over another medical device;
        one or more fluid infusion openings located at a distal end region of the catheter, the one or more fluid infusion openings configured to permit fluid to exit the catheter from the fluid lumen;
        one or more fluid holes located at the distal end region of the catheter, the one or more fluid holes configured to permit fluid to pass from the fluid lumen into the second lumen;
    an elongate member advanceable through the second lumen of the catheter, the elongate member having a temperature sensor disposed on a distal end portion thereof;
    wherein the temperature sensor is designed to shift between a first position where the temperature sensor is disposed within the second lumen of the catheter and is aligned with at least one of the one or more fluid holes in order to measure a temperature of fluid entering the second lumen of the catheter through the one or more fluid holes and a second position where the temperature sensor is disposed distal of the distal end of the catheter.

2. The catheter system of claim 1, wherein the one or more fluid infusion openings extend through a wall of the outer tubular member from an inner surface of the outer tubular member to an outer surface of the outer tubular member.

3. The catheter system of claim 2, wherein the one or more fluid infusion openings are configured to generate a jet of fluid exiting the catheter.

4. The catheter system of claim 1, wherein the one or more fluid holes extend through a wall of the inner tubular member from an outer surface of the inner tubular member to an inner surface of the inner tubular member.

5. The catheter system of claim 1, wherein the one or more fluid holes are one or more weeping holes configured to allow fluid to weep into the second lumen.

6. The catheter system of claim 1, wherein the one or more fluid infusion openings include four fluid infusion openings equidistantly spaced circumferentially around the outer tubular member.

7. The catheter system of claim 1, wherein the one or more fluid holes is a single weeping hole extending through the inner tubular member.

8. The catheter system of claim 1, wherein the catheter is a single-operator-exchange catheter in which the second lumen extends only through a distal portion of the catheter.

9. The catheter system of claim 1, wherein the second lumen extends through an entire length of the catheter.

10. The catheter system of claim 1, wherein another portion of the first lumen is defined by the outer tubular member.

11. A method of determining blood flow in a body vessel of a patient, the method comprising:
    advancing a catheter to a desired location within the body vessel, the catheter including an outer tubular member, an inner tubular member disposed within and axially fixed relative to the outer tubular member, a fluid lumen defined between the inner tubular member and the outer tubular member, and a second lumen defined by the inner tubular member, the second lumen having an open distal end such that the catheter is configured to be advanced over another medical device;
    delivering a fluid through the fluid lumen to a distal end region of the catheter;
    positioning a temperature sensor mounted on an elongate member within the second lumen of the inner tubular member so that a temperature sensor mounted on the elongate member is aligned with a fluid hole formed in a side wall of the inner tubular member;
    measuring the temperature of the fluid passing into the second lumen from the fluid lumen with the temperature sensor positioned in the second lumen;
    shifting the elongate member relative to the catheter so that the temperature sensor is positioned distally of the distal end region of the catheter;
    infusing the fluid into blood in the body vessel from the fluid lumen;
    measuring the temperature of a mixture of the fluid and the blood with the temperature sensor while the temperature sensor is positioned in the body vessel distal of the catheter; and
    calculating a blood flow rate based on the measured temperature of the fluid passing into the second lumen and the measured temperature of the mixture of the fluid and the blood.

12. The method of claim 11, wherein the catheter includes one or more fluid infusion openings located at the distal end region of the catheter, the one or more fluid infusion openings configured to permit the fluid to exit the catheter from the fluid lumen.

13. The method of claim 12, wherein the catheter includes one or more additional fluid holes located at the distal end region of the catheter, the one or more fluid holes configured to permit the fluid to pass from the fluid lumen into the second lumen.

* * * * *